(12) United States Patent
Chen

(10) Patent No.: US 11,745,024 B2
(45) Date of Patent: Sep. 5, 2023

(54) ELECTRICAL METHODS AND DEVICES FOR OPHTHALMIC TREATMENT

(71) Applicant: IRIDEX Corporation, Mountain View, CA (US)

(72) Inventor: Howard Chen, San Jose, CA (US)

(73) Assignee: IRIDEX Corporation, Mountain View, CA (US)

( * ) Notice: Subject to any disclaimer, the term of this patent is extended or adjusted under 35 U.S.C. 154(b) by 736 days.

(21) Appl. No.: 16/717,949

(22) Filed: Dec. 17, 2019

(65) Prior Publication Data

US 2020/0206521 A1 Jul. 2, 2020

Related U.S. Application Data

(60) Provisional application No. 62/785,576, filed on Dec. 27, 2018.

(51) Int. Cl.
| | |
|---|---|
| *A61N 1/40* | (2006.01) |
| *H05K 1/02* | (2006.01) |
| *A61B 3/14* | (2006.01) |
| *A61N 1/04* | (2006.01) |
| *A61B 5/0536* | (2021.01) |

(52) U.S. Cl.
CPC ............... *A61N 1/403* (2013.01); *A61B 3/14* (2013.01); *A61B 5/0536* (2013.01); *A61N 1/0472* (2013.01); *H05K 1/0277* (2013.01)

(58) Field of Classification Search
CPC .. A61N 1/403; A61N 1/0472; A61N 1/36046; A61B 3/14; A61B 5/0536; H05K 1/0277
See application file for complete search history.

(56) References Cited

U.S. PATENT DOCUMENTS

| | | | |
|---|---|---|---|
| 3,034,403 | A | 5/1962 | Neefe |
| 4,576,453 | A | 3/1986 | Borowsky |
| 4,732,148 | A | 3/1988 | L'Esperance, Jr. |
| 4,732,715 | A | 3/1988 | Bawa et al. |
| 4,966,452 | A | 10/1990 | Shields et al. |
| 5,108,388 | A | 4/1992 | Trokel |
| 5,135,466 | A | 8/1992 | Fedorov et al. |
| 5,147,284 | A | 9/1992 | Fedorov et al. |
| 5,376,086 | A | 12/1994 | Khoobehi et al. |
| 5,434,630 | A | 7/1995 | Bransome |

(Continued)

FOREIGN PATENT DOCUMENTS

| | | | |
|---|---|---|---|
| DE | 3535072 | 4/1987 | |
| WO | 0057773 A1 | 10/2000 | |
| WO | WO2017/223387 | * 12/2017 | ............... A61N 1/00 |

*Primary Examiner* — Amanda K Hulbert
*Assistant Examiner* — Philip C Edwards
(74) *Attorney, Agent, or Firm* — Kilpatrick Townsend & Stockton LLP

(57) ABSTRACT

A lens or eye mask for treating an eye of a patient includes a flexible printed circuit board (PCB) that is configured to fit over at least a portion of a surface of the eye and a plurality of electrode pairs that are arranged on the flexible PCB. An electrical source is configured to provide electrical energy to each electrode pair to create a near electromagnetic field within the eye and thereby therapeutically treat target tissue within the eye. A spacing between electrodes of each electrode pair is controlled to achieve a predetermined penetration depth of the near electromagnetic field within the eye.

5 Claims, 5 Drawing Sheets

(56) References Cited

U.S. PATENT DOCUMENTS

| | | |
|---|---|---|
| 5,697,923 A | 12/1997 | Poler |
| 5,719,656 A | 2/1998 | Bowling |
| 6,520,956 B1 | 2/2003 | Huang |
| 6,874,886 B2 | 4/2005 | Miller et al. |
| 7,321,795 B2 | 1/2008 | Bogdanowicz |
| 7,564,014 B2 | 7/2009 | Huh |
| 7,727,138 B2 | 6/2010 | Alvarado |
| 8,070,688 B2 | 12/2011 | Livne et al. |
| 8,287,592 B2 | 10/2012 | Silvestrini |
| 8,308,292 B2 | 11/2012 | Arai et al. |
| 8,527,055 B2 | 9/2013 | Rickard |
| 8,914,089 B2 | 12/2014 | Abreu |
| 9,138,142 B2 | 9/2015 | Christie et al. |
| 9,144,376 B2 | 9/2015 | Guth et al. |
| 2003/0109907 A1 | 6/2003 | Shadduck |
| 2005/0033420 A1 | 2/2005 | Christie et al. |
| 2006/0271026 A1 | 11/2006 | Silvestrini et al. |
| 2010/0076419 A1 | 3/2010 | Chew et al. |
| 2012/0209356 A1 | 8/2012 | Eckhouse et al. |
| 2013/0060306 A1 | 3/2013 | Colbauch |
| 2013/0123761 A1 | 5/2013 | Belkin et al. |
| 2014/0192311 A1 | 7/2014 | Pletcher et al. |
| 2015/0238357 A1 | 8/2015 | Goldberg et al. |
| 2015/0366706 A1 | 12/2015 | Belkin et al. |
| 2015/0374539 A1 | 12/2015 | Buzawa et al. |
| 2017/0007834 A1 | 1/2017 | Irazoqui et al. |
| 2017/0087014 A1 | 3/2017 | Potter et al. |
| 2018/0000337 A1 | 1/2018 | Chen et al. |
| 2019/0275326 A1* | 9/2019 | Irazoqui ................. A61N 1/025 |
| 2019/0344076 A1* | 11/2019 | Irazoqui ................. A61N 1/36 |

\* cited by examiner

ELECTRICAL METHODS AND DEVICES FOR OPHTHALMIC TREATMENT

CROSS-REFERENCE TO RELATED APPLICATIONS

The present application claims priority to Provisional U.S. Patent Application No. 62/785,576 filed Dec. 27, 2018, entitled "Electrical Methods and Devices for Ophthalmic Treatment," the full disclosure which is incorporated herein by reference in its entirety for all purposes.

The present application is related to U.S. application Ser. No. 15/892,893 filed Feb. 9, 2018, entitled "Method and Eye Mask Apparatus for Treating an Eye Using a Broad Area Light Source," the full disclosure which is incorporated herein by reference in its entirety for all purposes.

BACKGROUND OF THE DISCLOSURE

The present disclosure is generally related to medical systems, devices, and methods for treating a glaucomatous eye. Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Elevated intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via the Schlemm's canal into scleral plexuses and the general blood circulation. In open angle glaucoma there is reduced flow through the trabecular meshwork. In angle closure glaucoma, the iris is pushed forward against the trabecular meshwork, preventing the egress of fluid.

Uveoscleral outflow is a non-conventional pathway that is gaining importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical attempts to lower the production of aqueous humor by the ciliary processes. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, high intensity continuous wave (CW) infrared laser energy is directed through selected portions of the pars plicata region to the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam to a subsurface non-visible target such as the ciliary body can be challenging for a surgeon.

Conventional laser based surgical system use a single light source such as an edge emitting diode laser, diode pumped solid state laser, or fiber laser to treat glaucoma conditions. In such conventional systems, the light from a laser is transported by an optical waveguide (e.g., multi-mode fiber probe) to the site of the treatment in an eye. The probe used for glaucoma treatment typically touches the surface of the eye, with the laser source releasing pulsed energy at a target or treatment spot. The probe is then moved to a different target or treatment spot, typically in a clockwise or counterclockwise rotation around the edge of the eye, and the probe is then used again to release pulsed energy at the new target or treatment spot. This process is commonly referred to as "cyclo photocoagulation" for treating an eye.

While the prior systems, methods, and devices have provided advancements in the art, there is a need for improved systems that are less dependent on a physician or operator positioning and that are less dependent on expensive light sources and/or complex optical systems.

SUMMARY OF THE DISCLOSURE

Embodiments of the present disclosure generally relate to ophthalmic treatments that are provided by electrical currents that are generated within the eye. These treatments may be similar to those referred to as cyclophotocoagulation of the eye for the treatment of glaucoma. According to one aspect, a system for treating an eye of a patient includes a lens that is configured for positioning on the eye of the patient. The lens has an inner surface that is positionable against the eye and an outer surface that is opposite the inner surface. A first conductive component is positioned on the lens and a second conductive component is also positioned on the lens. The second conductive component is separated and electrically insulated from the first conductive component. The first conductive component and the second conductive component are positioned on the lens so that when the lens is positioned on the eye, the first conductive component or the second conductive component is positioned adjacent a limbus of the eye. The system also includes an electrical source that provides electrical energy to the first conductive component or the second conductive component to induce a current within the eye between the first conductive component and the second conductive component. The induced current delivers electromagnetic energy to target tissue within the eye to therapeutically treat the target tissue.

According to another aspect, a lens or eye mask for treating an eye of a patient includes a flexible printed circuit board (PCB) that is configured to fit over at least a portion of a surface of the eye and a plurality of electrode pairs that are arranged on the flexible PCB. An electrical source provides electrical energy to each electrode pair of the plurality of electrode pairs to create a near electromagnetic field within the eye that is effective to treat target tissue within the eye. A spacing between electrodes of each electrode pair is controlled to achieve a predetermined penetration depth of the near electromagnetic field within the eye.

According to another aspect, a method for treating glaucoma in an eye of a patient includes positioning a conductive component adjacent to a surface of the eye and providing electrical energy to the conductive component to induce a current within the eye and thereby deliver electromagnetic energy to target tissue within the eye to therapeutically treat the target tissue. The conductive component may be a loop conductor and the electrical energy may be provided to induce an inductive current within the eye. Alternatively, the conductive component may be a first conductive component and wherein the method may also include positioning a second conductive component adjacent to a surface of the eye so that the second conductive component is separated and electrically insulated from the first conductive component. The electrical energy may be provided to the first conductive component or the second conductive component to induce a resistive or capacitive current within the eye.

According to another aspect, a method for treating glaucoma in an eye of a patient includes positioning a mask or lens on a surface of the eye. The mask or lens has an inner surface that is positionable against the eye and an outer surface that is opposite the inner surface. A first conductive component is positioned on the mask or lens and a second conductive component is also positioned on the mask or lens. The first second conductive component is separated and electrically insulated from the first conductive component. The first conductive component and the second conductive component are positioned on the mask or lens so that when the mask or lens is positioned on the eye, the first conductive component or the second conductive component is positioned adjacent or radially outward form a limbus of the eye. The method also includes providing electrical energy to the first conductive component or the second conductive component to induce a current within the eye and thereby deliver electromagnetic energy to target tissue within the eye to therapeutically treat the target tissue.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Further details, aspects, and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE DISCLOSURE

Figure 1A:
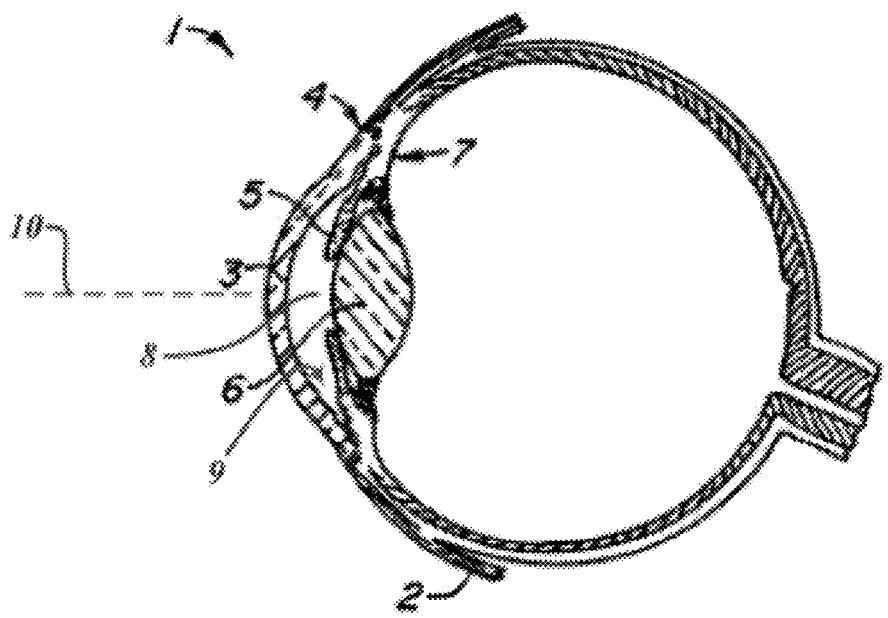
FIG. 1A shows the anatomy of an eye with relevant parts labeled to provide anatomical references.

Conventional ophthalmic laser systems typically employ a laser source, laser probe, power supply, and controller. The laser source, power supply, and/or controller may be components that are external to the laser probe or in some instances may be integrated into the laser probe. When the laser source is an external component, the laser probe generally contains an optical fiber and a connector for attachment to the laser source. The laser source is typically positioned within a console that is AC powered system and that is placed on a surface that is at least several feet away from a patient's eye. The laser energy is transported by an optical fiber (i.e., waveguide) to the patient's eye where photocoagulation based treatment takes place.

The laser energy is commonly provided via a single light source such as an edge emitting diode laser, diode pumped solid state laser, or fiber laser. The distal end of the laser probe typically touches the surface of the eye, with the laser source releasing pulsed energy at each spot before being moved to a different spot in a clockwise or counterclockwise rotation around the edge of the eye, which gives rise to the term "cyclophotocoagulation" for treating an eye. The manual process of moving a laser probe over the surface of an eye may be prone to issues such as scratching the surface of the eye. In addition, it may be difficult to precisely control the location and positioning of the probe about the eye and thus, it may be difficult to precisely control the delivery of the laser light to the eye, which may lead to inconsistent treatments.

The embodiments described herein do not employ laser energy in treating the eye. Rather, the embodiments herein deliver electromagnetic energy to the tissue of the eye to provide a therapeutic treatment. In a specific embodiment, electromagnetic energy may be delivered to the ciliary body for glaucoma treatment. More specifically, the electromagnetic energy may be delivered to reduce intraocular pressure.

It is known that the aqueous humor is produced by the ciliary body by processes related to the cell membrane for the cells contained in the ciliary body. It is also known that cell membrane processes typically involve ion currents such as the Na—K pump. It is possible to interfere with and/or alter these ion currents by the application of external electrical currents and thus, it is possible to affect the ciliary body associated ion currents by the application of electrical means. The treatment of the tissue by the applied electromagnetic energy may result from heating of the tissue. An intensity of the electromagnetic energy and/or a duration of the application may be controlled to achieve a desired heat response of the targeted tissue, which may allow a physician to achieve a desired therapeutic response. Heating the tissue through electromagnetic energy may provide a more direct and targeted approach than conventional systems that employ laser light energy. For example, the position of the electrodes on or about the eye may be precisely controlled so that the electromagnetic energy is directly delivered to, and directly affects, the targeted tissue. This may result in less electromagnetic energy being delivered to and/or affecting non-targeted collateral tissue that surrounds, or is adjacent to, the targeted tissue.

The energy may be delivered to the eye via one or more electrodes that are positioned on or adjacent to the eye. In some embodiments, the one or more electrodes may be individual components that are positioned on the eye or directly adjacent to the eye. In other embodiments, the one or more electrodes may be components that are positioned on a mask or other material that is in turn positioned on the eye, such as a specialty contact lens. The electromagnetic energy may be delivered to the eye via the one or more electrodes in a resistive, capacitive, or inductive manner. The positioning of the electrodes on or about the eye may be determined and controlled so that the electromagnetic energy is precisely delivered to the targeted tissue. For example, near field currents may be created that directly target and affect the targeted tissue and that do not substantially affect non-targeted surrounding tissue. While various features of the embodiments have been described generally, additional features and aspects of the embodiments will be more apparent in reference to the various figures described herein below.

FIG. 1A shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6, and the ciliary body and related processes 7. The anterior chamber is a fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. The eye 1 also has a visual/optical axis 10.

Figure 1B:
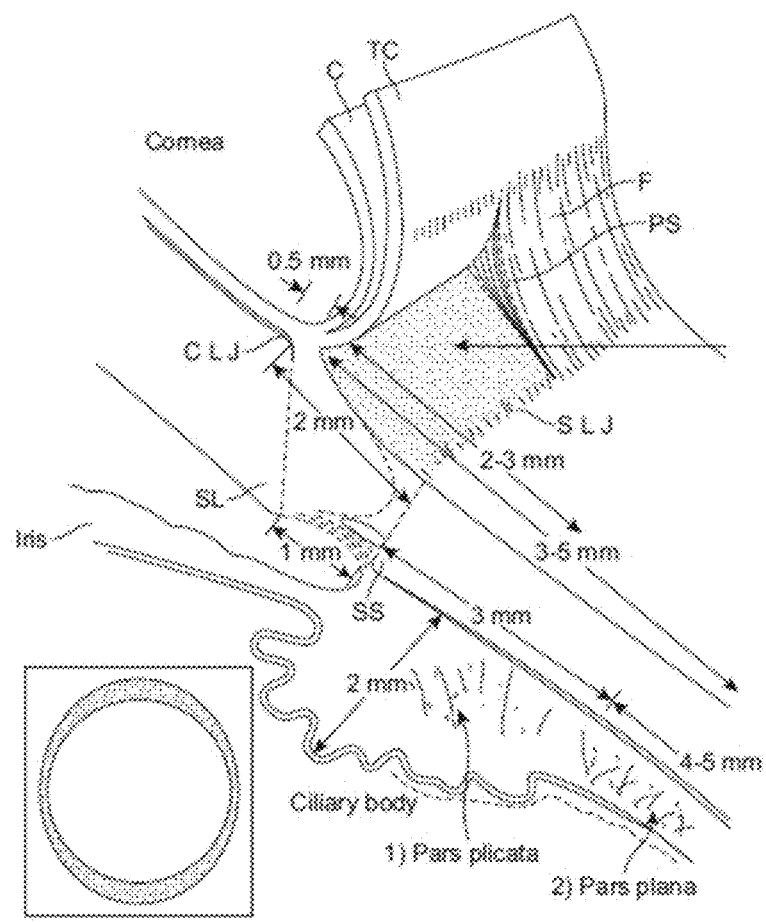
FIG. 1B shows further details of the eye anatomy.

FIG. 1B shows further details of the surgical eye anatomy. Embodiments described herein may target intraocular structures that span from the posterior pars plicata to the pars plana. Alternatively, the pars plana may be targeted and the pars plicata, ciliary body, and other ciliary processes avoided.

Figure 2:
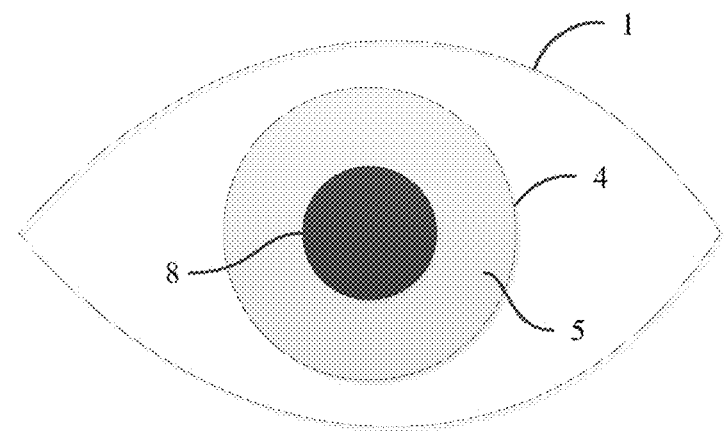
FIG. 2 illustrates a schematic drawing of an eye.
Figure 3:
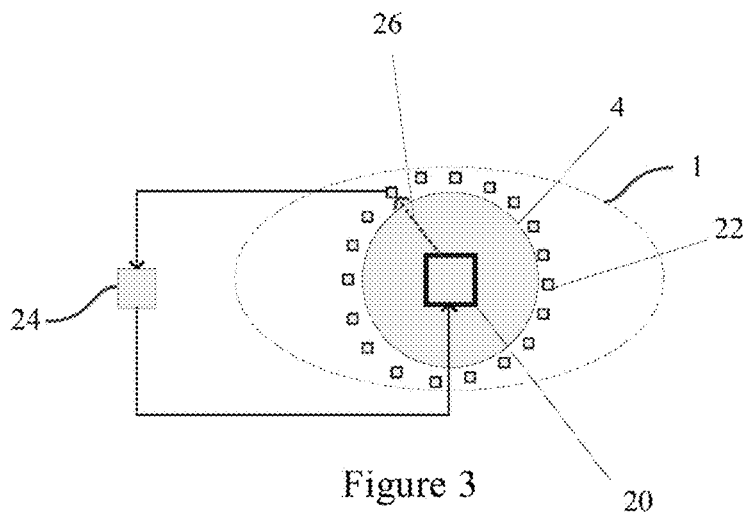
FIG. 3 illustrates a system that is configured to treat an eye by delivering electromagnetic energy to the eye.

FIG. 2 illustrates a simplified front view of the eye 1. Specifically, FIG. 2 illustrates the pupil 8, the iris 5, and the limbus 4 of the eye 1. FIG. 3 illustrates a system that is configured to treat the eye 1 by delivering electromagnetic energy to the eye 1. The system includes a first conductive component or electrode 20 that is positioned on the eye 1 and a second conductive component or electrode 22 that is positioned on the eye 1. As illustrated, the system typically includes a plurality of the second electrodes 22, which may also be referred to as edge electrodes, that are positioned near the eye's limbus. The second electrodes 22 may be spaced circumferentially around the limbus 4 and spaced slightly radially outward from the limbus 4. In some embodiments, the second electrode is positioned between 0 and 5 mm posterior to the limbus 4, although in other embodiments, the second electrode is positioned between 1 and 5 mm or between 1 and 4 mm posterior to the limbus 4. The second electrodes 22 are separated from the first electrode 20, which in the illustrated embodiment is positioned relatively centrally about the eye over the pupil 8. In some embodiments, the second electrodes 22 may be separated from the first electrode 20 by between 0.1 and 10 mm. The first electrode 20 may also be referred to as a central electrode. An electrical source 24 is electrically coupled with the first electrode 20 and with each one of the second electrodes 22. In FIG. 3, the electrical source 24 is illustrated as being electrically coupled with a single second electrode 22, but a person of skill in the art will readily recognize that the electrical source 24 could be electrically coupled with each second electrode 22. The first electrode 20 and/or the second electrode 22 may be relatively small components. The first electrode 20 and the second electrode 22 may be roughly equal in size or may differ in size based upon a required application of the electrodes or for any other reason. In some embodiments, the first electrode 20 and/or second electrode 22 may be between 0.1 and 5 mm in size. In a specific embodiment, the first electrode 20 and/or second electrode 22 may be approximately 0.5 mm in size. The electrical source 24 could be an external power source 24, such as a power source that is electrically connected to the first electrode 20 and the second electrodes 22 via a wire; or the electrical source 24 could be a wirelessly powered device that is positioned on a mask or lens.

The electrical source 24 is configured to provide electrical energy to the first electrode 20 and the second electrode 22 to induce a current 26 within the eye 1 between the first electrode 20 and the second electrode 22. In this manner, electromagnetic energy may be delivered to target tissue within the eye 1 in order to therapeutically treat the target tissue of the eye 1. Specifically, an electrical conduction current 26 follows a voltage drop defined by the first electrode 20 and the second electrode 22. In the eye 1, the ciliary body and related tissue (e.g., ciliary muscle, ciliary processes, etc.) are distributed around the cornea 3 near the limbus 4, which makes it possible to use a cornea contact electrode (i.e., first electrode 20) and numerous second electrodes 22 to define current paths that target and treat the ciliary body and/or related tissue.

In order to further define the current path, the electrical source 24 is programmed to electrically couple with individual second electrodes 22 in a sequential manner or any other desired manner. This induces a voltage drop between the first electrode 20 and a selected or identified one of the second electrodes 22, which results in the electrical conduction current 26 following a defined and desired path within the eye 1. In addition, the electrical source 24 may control the voltage drop between the first electrode 20 and any of the second electrodes 22 as desired to individually control the voltage drop between the pair of electrodes and thereby control the magnitude of the electrical conduction current that is induced between the pair of electrodes. The current that is induced by the electrical source 24 may be either AC or DC depending on the desired treatment and/or any other factor. In some instances, the electrical source 24 may simultaneously electrically couple with two or more second electrodes 22 in order to simultaneously treat multiple regions of the eye 1.

In some embodiments, the first electrode 20 and the second electrodes 22 may be individual components that are positioned on the eye or positioned directly adjacent to the eye. In such embodiments, the second electrodes 22 may be positioned on or adjacent the sclera 2, or the second electrodes 22 may be positioned under the sclera 2. In other embodiments, the first electrode 20 and/or the second electrodes 22 may be positioned on a mask or other material that is in turn positioned on the eye. In a specific embodiment, the mask may be a disposable lens that may be positioned on the surface of the eye 1. The lens may have an inner surface that is positionable against the eye 1 and an outer surface that is opposite the inner surface. The first electrode 20 and/or second electrodes 22 may be positioned on the inner surface of the outer surface of the lens so that when the contact lens is positioned on the eye, the first electrode 20 and the second electrodes 22 are positioned about the eye as described above. The lens may be, or include, a flexible printed circuit board type material. The electrical source 24 could also be positioned on the lens. In such embodiments, the electrical source 24 may be wirelessly powered or may include one or more wires that electrically connect to an external device.

The lens may also include other components, such as microprocessors, an RFID, one or more sensors, a memory chip, a special mechanical attachment mechanism, solar components that generate electrical power, and the like. The use of an RFID may allow the system to recognize an orientation of the lens about the eye and to adjust the parameters of the therapeutic treatment based on these parameters. The sensor(s) may be used to measure or detect various conditions within the eye and to communicate this information with a processing device in order to allow the therapeutic treatment to be tailored or adjusted to most effectively treat the eye 1. For example, the sensor(s) may measure the intraocular pressure before, during, and/or after the treatment to allow the voltage or energy application duration to be adjusted and/or to determine an effectiveness of the treatment. The memory chip may store relevant information and communicate this information to one or more components of the system, such as a microprocessor or an external processing device.

The number of second electrodes 22 that are used corresponds to a number of targeted sites that are determined to be effective to treat the eye 1. For example, in some embodiments it may be desirable to treat only 5 areas around the eye whereas in other embodiments it may be desirable to treat 40 or more areas around the eye. The system of FIG. 3 commonly includes between 5 and 40 second electrodes 22 that are positioned around the limbus 4 and typically evenly spaced circumferentially around the limbus 4 in an annular like configuration. In other embodiments the system may include between 10 and 30 second electrodes 22, and more commonly between 15 and 25 second electrodes 22. In a specific embodiment, the system may include approximately 20 second electrodes 22.

The electromagnetic energy that is delivered to the eye 1 via the electrical conduction current 26 therapeutically treats the tissue typically by heating the tissue. Specifically, the eye tissue that is disposed along a path of the electrical conduction current 26 has a determinable resistance that opposes the electrical conduction current 26. Thus, inducing the electrical conduction current 26 results in heating of the tissue within the eye along the path. A calculated or determined amount of electromagnetic energy may be applied to heat the tissue by a desired amount that is determined to therapeutically treat the eye tissue. A normal temperature of the eye tissue is approximately 98 degrees Fahrenheit. 127 degrees Fahrenheit is an estimated temperature at which tissue damage will occur. Therefore a maximum heating of the eye tissue should not exceed 29 degrees Fahrenheit in order to avoid permanent damage to the eye tissue. Accordingly, electromagnetic energy may be applied to heat the eye tissue to between 1 and 25 degrees Fahrenheit, although a temperature rise of between 1 and 20 degrees or between 1 and 15 degrees Fahrenheit is more common. In a specific embodiment, the tissue of the eye 1 may be heated by between 1 and 10 degrees Fahrenheit, between 2 and 10 degrees Fahrenheit, between 1 and 5 degrees Fahrenheit, between 1 and 4 degrees Fahrenheit, or between 2 and 4 degrees Fahrenheit. In a specific embodiment, the therapeutic treatment that is provided is effective to reduce an intraocular pressure of the eye 1, such as for treatment of glaucoma.

In some embodiments, the first electrode 20 and the second electrodes 22 may provide between 0.1 and 1.0 Watts of electrical power, although between 0.3 and 0.7 W is more common. In a specific embodiment, the first electrode 20 and the second electrodes 22 may provide 0.4 to 0.6 W, or 0.4 to 0.5 W, of electrical power.

The use of the system illustrated in FIG. 3, and the systems illustrated and described elsewhere herein, may eliminate the need for laser treatment probes and laser light sources to be employed in therapeutically treating the eye. In other embodiments the system of FIG. 3, and the systems illustrated and described elsewhere herein, may be used in conjunction with a laser treatment probe and laser light source to therapeutically treat the eye.

Figure 4:
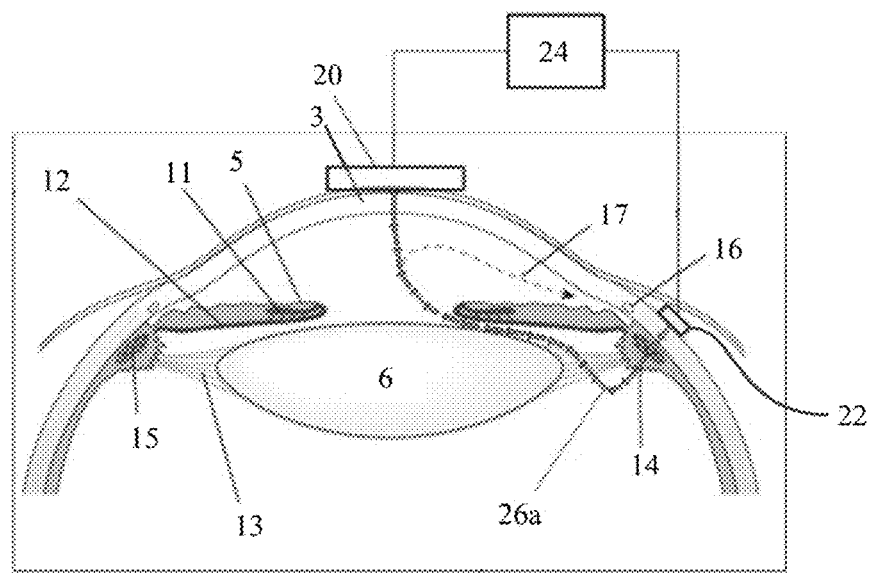
FIG. 4 illustrates a use of the system of FIG. 3 to deliver a resistive conduction current through eye tissue.

Referring to FIG. 4, illustrated is a use of the system of FIG. 3 to deliver a resistive conduction current 26a through the tissue of the eye 1 between the first electrode 20 and one of the second electrodes 22. FIG. 4 shows a typically path 17 of the aqueous humor as it flows from the ciliary body 14 toward the Schlemm's canal 16. The first electrode 20 is positioned atop the cornea 3 and the second electrode 22 is positioned adjacent the ciliary body 14, although the second electrode 22 may be positioned elsewhere, such as near the Schlemm's canal 16, as desired or required based upon a given application of the system. The voltage drop that is produced between the first electrode 20 and the second electrode 22 causes a resistive circuit to form, which produces the resistive conduction current 26a. The resistive conduction current 26a follows the flow of the aqueous humor. Specifically, the resistive conduction current 26a flows from the second electrode 22 through the suspensory ligaments 13, over the lens 6, around the iris 5, and to the first electrode 20.

The resistive conduction current 26a causes tissue within the eye 1 to heat up. For example, the ciliary body 14, ciliary processes, and/or ciliary muscle 15 may heat up as the current 26a flows through the tissue. In other embodiments, the second electrode may be positioned to heat up other tissue within the eye 1, such as tissue adjacent to the Schlemm's canal 16. Minimal heating may be experienced in other tissue within the eye, such as the constrictor muscle 11, dilator muscle 12, and the like.

The first and second electrodes, 20 and 22, are conductively attached to the surface of the eye 1 at the respective locations. Conductively attaching the first and second electrodes, 20 and 22, to the eye may be achieved in a variety of way, including the use of metal electrodes and/or the use of a conductive gel between the eye tissue and the electrodes. In such embodiments, the conductive gel may contain chemicals for various treatment purposes, such as temporary anesthesia of the eye tissue. Other methods of conductively attaching the electrodes to the eye may also be employed.

The electrical source 24 can be implemented and controlled according to various methods. For example, a software controlled current source may be used to flow a predefined level of electrical current through the eye tissue that is able to compensate for the individual impedance variations of the eye 1. In some embodiments, the electrical source 24 may be capable of measuring the electrical impedance of the eye 1 via the first electrode 20, the second electrode 22, or one or more sensors (not shown). In such embodiments, a detailed electrical impedance tomography image can be obtained after one or more current paths are evaluated. The electrical impedance tomography image may be evaluated for further medical analysis of the eye and/or for analysis of the therapeutic treatment.

Figure 5:
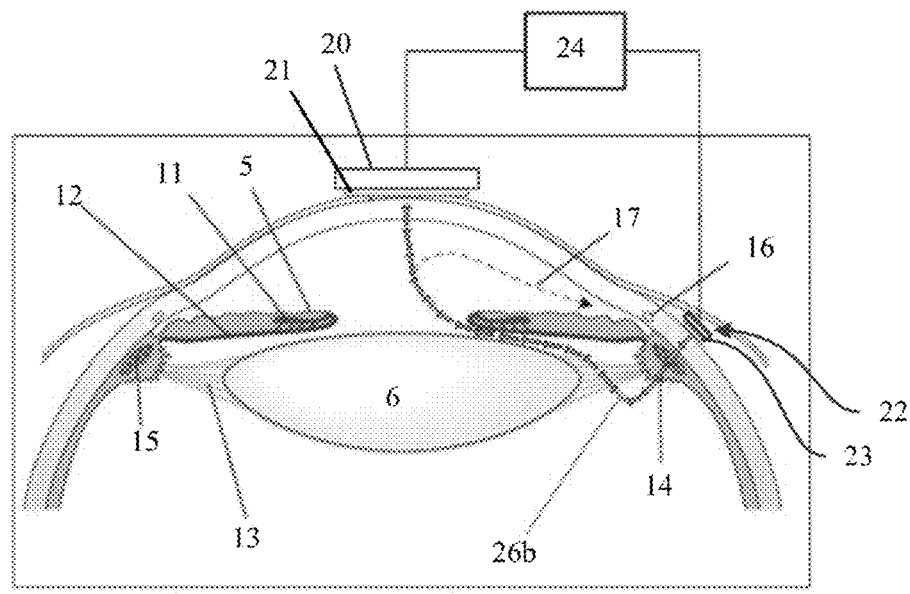
FIG. 5 illustrates a use of the system of FIG. 3 to deliver a displacement or capacitive current through eye tissue.

Referring to FIG. 5, illustrated is another use of the system of FIG. 3 in which the first electrode 20 and the second electrode 22 are insulated from the eye 1 so that the electrodes function as capacitors to deliver a displacement or capacitive current through the tissue of the eye 1 between the first and second electrodes. Specifically, a first insulative material 21 is positioned between the first electrode 20 and the eye tissue and a second insulative material 23 is positioned between the second electrode 22 and the eye tissue. Although not illustrated, it should be realized that an insulative material could be placed between the eye tissue and each of the second electrodes 22 illustrated in FIG. 3 so that the first electrode 20 and each of the second electrodes 22 function as capacitors.

In the illustrated embodiment, the first electrode 20 and the second electrode 22 form a capacitor with the eye tissue between the electrodes functioning as the dielectric. In such embodiments, the eye tissue interacts with an AC electric field such that a displacement or capacitive current 26b is produced by AC voltage across the first and second electrodes, 20 and 22. The capacitive method illustrated in FIG. 5 differs from the conductive current method illustrated in FIG. 4 in that no Ohmic contact is required between the electrodes and the eye tissue. The capacitive method illustrated in FIG. 5 may be preferred in some instances since it could be difficult to maintain Ohmic contact in some patients, such as patients with advanced glaucoma or other conditions that might result in large contact resistance differences.

As with the conductive method, the displacement current 26b may follow the flow of the aqueous humor within the eye. Specifically, the displacement current 26b may flow through the suspensory ligaments 13, over the lens 6, and around the iris 5. In other embodiments, the position of the second electrode 22 and the second insulative material 23 may be adjusted so that the displacement current 26b flows elsewhere through the eye tissue, such as adjacent to the Schlemm's canal. The displacement current 26b causes tissue within the eye 1 to heat up. For example, the ciliary body 14, ciliary processes, and/or ciliary muscle 15 may heat up as the displacement current 26b flows through the tissue. In other instances, the tissue adjacent to the Schlemm's canal 16 may heat up due to the displacement current 26b. Minimal heating may be experienced in other tissue within the eye, such as the constrictor muscle 11, dilator muscle 12, and the like.

In some embodiments, the capacitive method illustrated in FIG. 5 could be optimized in a frequency domain using unlicensed ISM frequency bands, such as 13.56 MHz. The electromagnetic fields with a capacitive applicator are complex in nature with both electric and magnetic field components and may be optimized for specific treatment requirements. In some embodiments, the capacitive system can be controlled and set to deliver between 0.1 and 1.0 W, or between 0.3 and 0.7 W, of electrical power to the eye tissue. In another embodiment, the capacitive system can be controlled and set to deliver between 0.4 to 0.6 W, or between 0.4 to 0.5 W, of electrical power to the eye tissue. The capacitive system may incorporate sensors in a feedback loop in order to enable the system to self-adjust, or semi self-adjust, in order to ensure that the desired amount of electrical power is delivered to the eye tissue.

Figure 6:
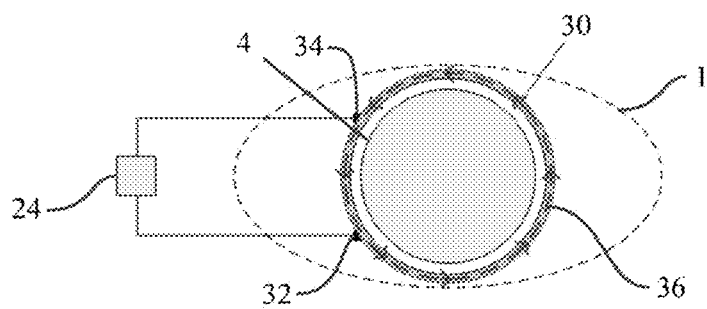
FIG. 6 illustrates another system that is configured to treat an eye by delivering electromagnetic energy to the eye.

FIG. 6 illustrates another system that is configured to treat the eye 1 by delivering electromagnetic energy to the eye 1. In the system of FIG. 6, the first and second electrodes, 20 and 22, are replaced with a loop antenna or conductor 30. The loop conductor 30 is electrically coupled with the electrical source 24 (i.e., AC electrical source), which induces an inductive current 36 to flow within the loop conductor 30, which in turn produces or delivers a near electromagnetic field within the eye. In some embodiments, the electrical source 24 may be electrically coupled with the loop conductor via a pair of contacts, 32 and 34. In other embodiments, the loop conductor 30 may be wirelessly coupled with the electrical source 24 so that the inductive current 36 is induced wirelessly, such as by changing the magnetic field via the electrical source 24.

As illustrated in FIG. 6, the loop conductor 30 may have a diameter that is slightly larger than a diameter of the limbus 4 so that an inner edge of the loop conductor 30 is positioned radially outward from the limbus 4. In other embodiments, the diameter of the loop conductor 30 may be roughly equivalent to the diameter of the limbus or may be slightly smaller than the diameter of the limbus. The size of the loop conductor 30 may be varied so that the loop conductor 30 is positioned immediately adjacent to tissue that is to be treated with the inductive system. In some instances, the loop conductor 30 is a separate component that is positioned on or directly adjacent to the eye 1. In other embodiments, the loop conductor 30 is implemented as a trace on a lens that is positioned on the surface of the eye 1.

Figure 7:
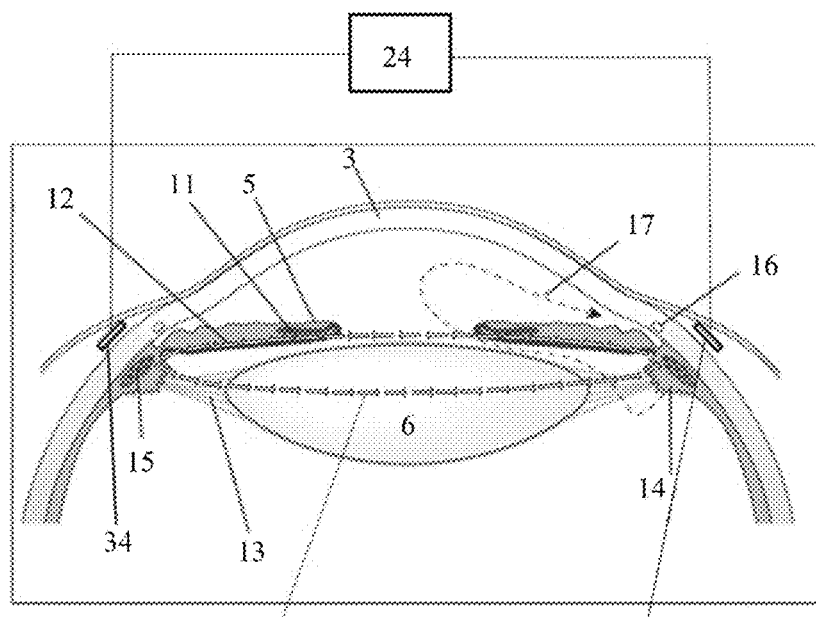
FIG. 7 illustrates a use of the system of FIG. 6 to deliver an inductive current through eye tissue.

As illustrated in FIG. 7, the inductive system of FIG. 6 uses Faraday's law to create inductive currents 36 that counter the change of the magnetic flux through the loop conductor 30 that is connected to the electrical source 24. In this manner, the inductive system produces a magnetic tissue stimulation in which the near field is contained approximately in the radius defined by the size of the loop conductor 30, and more specifically, the near field is confined to the volume of the eye 1. Additionally, the inductive current 25 flows in approximately the same plane as the loop conductor 30 with the magnitude of the magnetic flux being highest in the tissue regions nearest the loop conductor 30.

The inductive current 36 causes tissue within the eye 1 to heat up, which may cause a biological effect as described herein that beneficially treats or affects the eye 1. Specific tissue within the eye 1 may be targeted by ensuring that the loop conductor 30 is positioned on the eye so that the targeted tissue is aligned with the plane of the loop conductor 30. The voltage that is applied by the electrical source 24 and/or the frequency of the alternating current may be selected so that the induced current 36 targets and directly affects the targeted tissue. For example, as illustrated in FIG. 7, the current 36 is induced so that it most directly affects the ciliary body 14, ciliary processes, and/or ciliary muscles 15. The current 36 may have a lesser effect on other tissue within the eye 1 that is not positioned within the plane of the loop conductor 30, such as the constrictor muscle 11, dilator muscle 12, and the like. In other embodiments, the loop conductor 30 may be positioned to more directly affect the Schlemm's canal 16 or essentially any other desired tissue within the eye 1.

Figure 8:
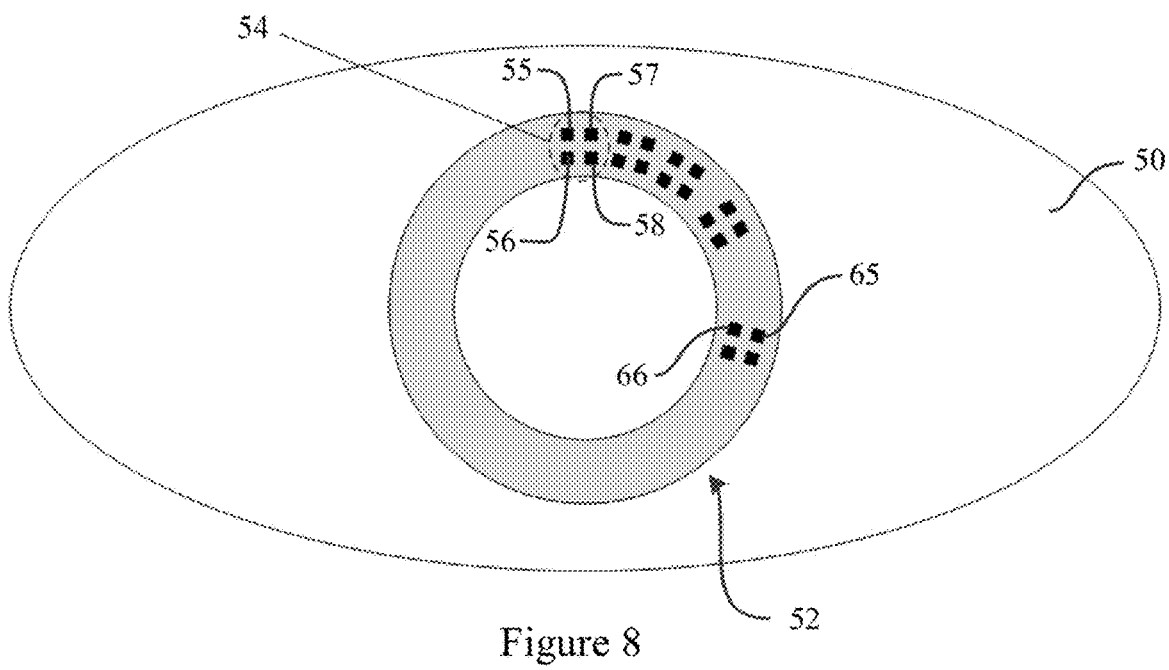
FIG. 8 illustrates a flexible printed circuit board having an annular shape that may be positioned directly on the eye or that may be positioned on a lens that is positioned on the eye.

FIG. 8 illustrates a flexible printed circuit board 52 having an annular shape that may be positioned directly on the eye 1 or that may be positioned on a lens 50 that is positioned on the eye 1. While the flexible printed circuit board 52 is illustrated having an annular or circular shape, it should be realized that any other geometric shape may be employed, and in particular oval or elliptical shapes. In a preferred embodiment, a plurality of electrodes are positioned on the flexible printed circuit board 52. The plurality of electrodes may be used in a resistive or capacitive manner as described above. In another embodiment, a loop conductor may be positioned on the flexible printed circuit board 52 so that the flexible printed circuit board 52 may be used in an inductive manner. For ease in describing the embodiment, the disclosure will focus on the flexible printed circuit board 52 including electrodes rather than a loop conductor.

The plurality of electrodes are arranged so that when the flexible printed circuit board 52, or lens 50, is positioned on the eye, the electrodes are positioned above a desired treatment area, such as above the Schlemms' canal or the ciliary body. Each of the electrodes is connected with an electrical source (not shown) via a wired or wireless connection as described herein. The electrical source may be positioned external to the flexible printed circuit board 52 and/or lens 50, or may be positioned on the flexible printed circuit board 52 or lens 50 as desired.

The electrical source is configured to activate a pair of electrodes of the plurality of electrodes in order to induce a resistive or capacitive current within the eye 1. For example, a first electrode 55 may be configured to work cooperatively with a second electrode 56 and both electrodes may be electrically activated by the electrical source to produce a voltage drop that results in a resistive or capacitive current being induced between the first and second electrodes, 55 and 56. When the electrodes are used in a capacitive manner, an insulative material is positioned between the electrodes and the eye tissue. In such embodiments, the flexible printed circuit board 52 may function as the insulative material between the electrodes and the eye tissue, or the electrodes may be coated with an insulative material. The arrangement of the electrodes on the flexible printed circuit board 52 as illustrated in FIG. 8 may be particularly useful when a capacitive current is induced to treat the eye.

The electrical source may activate electrode pairs individually (i.e., activate electrodes 55 and 56 in isolation), or the electrical source may activate multiple electrode pairs simultaneously, such as simultaneously activating a first electrode pair (i.e., electrodes 55 and 56) and a second electrode pair (i.e., electrodes 65 and 66).

The electrodes are typically paired in a radial manner so that the electrode pair includes both an outer electrode (i.e., first electrode 55) and an inner electrode (i.e., second electrode 56). The electrodes are arranged so that a radial gap exists between the outer electrode and the inner electrode. In such embodiments, the resistive or capacitive current is induced in a radial direction between the inner and outer electrodes. In other embodiments, the electrodes may be paired in a circumferential manner so that the electrode pair includes a first circumferential electrode (i.e., first electrode 55) and a second circumferential electrode (i.e., third electrode 57). The electrodes are arranged so that a circumferential gap exists between the first circumferential electrode and the second circumferential electrode. In such embodiments, the resistive or capacitive current is induced in a circumferential direction between the first and second circumferential electrodes. In such embodiments, the flexible printed circuit board 52 may not include an inner set of electrodes. If the flexible printed circuit board 52 does include an inner set of electrodes, the inner set of electrodes may also be circumferentially paired so that a circumferentially directed resistive or capacitive current is induced within the eye tissue via both the inner set of electrodes and the outer set of electrodes. In yet another embodiment, the system may be designed to employ both radially oriented and circumferentially oriented electrodes in delivering the therapeutic treatment. For example, a pair of circumferential electrodes (i.e., electrode 55 and electrode 57) may be used to deliver a resistive or capacitive current to the eye tissue and then a pair of radial electrodes (i.e., electrode 55 and electrode 56) may be used to deliver a resistive or capacitive current to the eye tissue.

Figure 9:
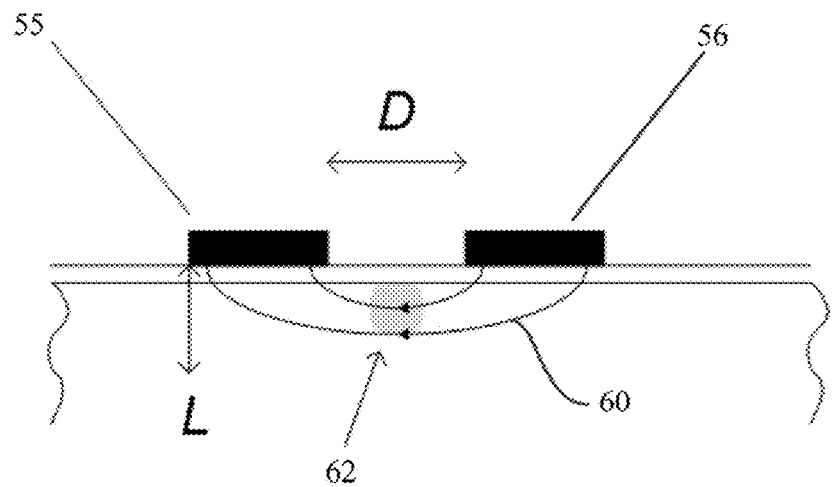
FIG. 9 illustrates how an electrode pair may be arranged to control a penetration of a near electromagnetic field into eye tissue.

FIG. 9 illustrates how the electrode pair may be arranged to control the penetration of a near electromagnetic field into the eye tissue. Specifically, the radial or circumferential gap or spacing distance D between the first electrode 55 and the second electrode 56 (or third electrode 57) may be controlled to achieve a desired penetration or depth L of the near electromagnetic field into the eye. The extent of the near electromagnetic field penetration L into the eye can be controlled by the spacing distance D between two adjacent electrodes since the near electromagnetic field follows a $1/r^n$ attenuation. The $1/r^n$ attenuation results in the near electromagnetic field attenuating or dropping off at multiple powers of the inverse of the distance from the electrodes.

In the instant embodiment, r would be roughly equal to the distance from the printed circuit board-eye tissue interface. The result is that the near electromagnetic field can be confined to a penetration depth L that is roughly equal to the spacing D between the electrodes, or stated differently, L D. In terms of arranging the electrode pairs on the flexible printed circuit board 52, the distance D between the electrodes can be selected to achieve a roughly equivalent penetration of the near electromagnetic field into the tissue, which provides a simple way to lay out the flexible printed circuit board 52 so that localized electrocoagulation or heating can be achieved.

As further illustrated in FIG. 9, the near electromagnetic field induces a capacitive or resistive current 60 to flow within the tissue, which causes localized heating and electrocoagulation 62 of the tissue and thereby provides the therapeutic effects described herein. In some embodiments, the distance D between the electrodes may be between 0.1 and 5 mm, although a distance of between 1 and 5 mm, or between 1 and 4 mm, is more common. For glaucoma treatments, the near electromagnetic field needs to penetrate through the sclera and to the ciliary body or ciliary processes. The sclera is mainly an insulator and has a thickness range of between 0.6 and 1.2 mm. The penetration depth L should approximately match the thickness of the sclera and thus, the penetration depth L should be at least 0.5 or 0.6 mm and is commonly designed to be between 0.5 and 1.5 mm. In a specific embodiment, the penetration depth L is approximately 0.6 to 1.2 mm, and more specifically approximately about 1.0 mm. To achieve this penetration depth, the spacing D between the electrodes (e.g., electrodes 55 and 56) is typically at least 0.5 mm and is more commonly between 0.5 and 1.5 mm. In a specific embodiment, the spacing D between the electrodes is approximately 0.6 to 1.2 mm, and more specifically approximately about 1.0 mm. The spacing D between the electrodes described herein helps to ensure that localized heating and/or localized electrocoagulation 62 of the ciliary body or ciliary processes is achieved. The size of the electrodes may be roughly 0.5 mm. This treatment may result in similar treatments that are achieved via laser treatment probes that employ 810 nm lasers.

In contrast to some conventional systems that provide stimulating energy to hyperpolarize the non-pigmented epithelium of the ciliary body, in the instant embodiments the electrical energy is targeted at the pigmented cells of the ciliary body, which respond to light energy. For example, some conventional systems focus on nerve stimulation rather than targeting pigmented cells of the ciliary body. Employing bio-electromagnetism to stimulate nerves or produce a nerve response in the eye, however, may be insufficient to induce localized heating of the eye tissue in a manner that would be effective to treat the eye as described herein. Specifically, employing bio-electromagnetism to stimulate nerves within the eye may not involve delivering large currents to the tissue that would be required to produce a heating of the tissue that is sufficient to therapeutically treat the eye.

In some instances the electrodes described herein may be used as both a diagnostic tool and a therapeutic treatment tool. For example, electrical impedance tomography (EIT) may be used to map a tissue's electrical impedance due to the ability of blood vessels to conduct currents. Electrical impedance tomography may be performed for the entire area under the sclera including the area under the cornea. Electrical impedance tomography may be performed using the electrodes as both transmitters and receivers of electrical signals. The electrodes may be connected to digital signal processors in order to process the data and map the eye tissue. For example, when an array of electrodes illustrated in FIG. 8 are used, the linear set of equations of $\{v\}=\{i\}*\{Z\}$, where Z is the complex impedance matrix, will yield a simplified impedance tomogram that could be used for any treatment. The electrical impedance tomogram may be useful as a diagnostic tool for glaucoma since the vitreous humor fluid path is often altered leading to higher IOP pressure, which could result in a change from normal electrical impedance traced to fluid distribution. Conventional systems that are designed to stimulate nerves within the eye are not configured to both construct an electrical model of the eye and to conduct treatment.

Referring again to FIG. 8, in some embodiments an electrode pair may be used to deliver the therapeutic treatment and one or more sensors or sensory electrodes may be used to measure one or more properties of the eye, such as the bio-impedance of the eye. For example, the first and second electrodes, 55 and 56, may be used to deliver a capacitive or resistive current within the eye as described herein, while a third sensory electrode 57 and/or fourth sensory electrode 58 may be used to measure a response to the delivered capacitive or resistive current, such as by measuring the bio-impedance or another property of the eye. In some embodiments, the third sensory electrode 57 and/or fourth sensory electrode 58 may not be electrodes, but may be other sensors that are able to sense or measures conditions or properties within the eye.

The first electrode 55, second electrode 56, third sensory electrode 57, and/or fourth sensory electrode 58 may form an electrode group 54 that is essentially able to simultaneously provide an electrical energy based treatment and to measure an effectiveness of the treatment in real time. The electrode group 54 may be employed in a feedback loop to determine a temperature rise in the eye tissue and to allow the procedure to be tweaked or adjusted in real time to achieve a desired treatment outcome or goal.

While FIG. 8 shows approximately 20 electrodes being positioned around roughly a quarter of the flexible printed circuit board 52's circumference. It should be understood that the electrodes are more commonly positioned around the entire circumference of the flexible printed circuit board 52 with electrode pairs (e.g., electrodes 55 and 56), or electrode groups 54, evenly spaced circumferentially around the flexible printed circuit board 52 and evenly spaced apart from adjacent electrode pairs or groups. The size of the electrodes are also typically small, such as between 0.1 and 5 mm, and more commonly between 0.5 and 5 mm.

The flexible printed circuit board 52 may have any number of electrodes spaced around the flexible printed circuit board 52. Each electrode pair represents a single treatment spot or position for the delivery of electrical energy to the eye. In some embodiments, the flexible printed circuit board 52 or lens may be configured to treat between 5 and 40 separate positions or spots on the eye, which results in the flexible printed circuit board 52 or lens 50 including between 10 and 80 electrodes. In other embodiments, the flexible printed circuit board 52 or lens 50 may be configured to treat between 10 and 30 positions or spots or between 15 and 25 positions or spots on the eye, which corresponds the flexible printed circuit board 52 or lens 50 including between 20 and 60 electrodes or between 30 and 50 electrodes, respectively. In a specific embodiment, the flexible printed circuit board 52 or lens 50 is configured to treat approximately 20 positions or spots on the eye, which results in the flexible printed circuit board 52 or lens including approximately 40 electrodes.

Since the electrode pairs are positioned closer together in FIG. 8 than in FIG. 3, the electrical power that is applied to the electrode pairs and/or the duration of the application may vary slightly from the electrical power and duration previously described for the resistive and capacitive embodiments. In some embodiments, a constant current source is used to drive the electrical impedance in the tissue between the electrodes in FIG. 8. In such embodiments, the output voltage of the current source may be raised to a level that is required to provide a specified current.

Figures 10, 11:
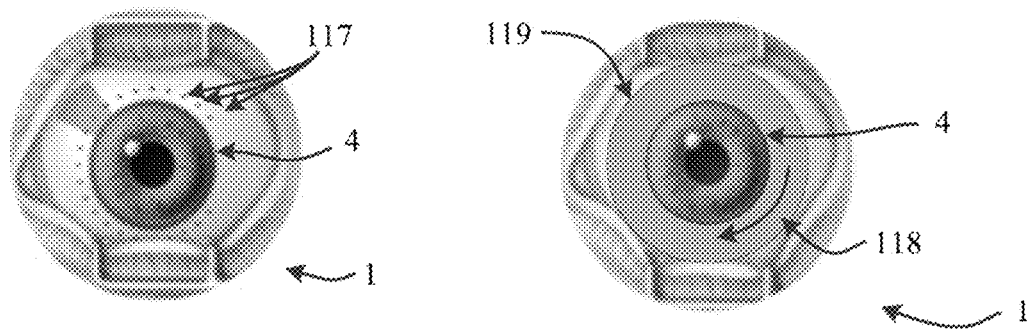
FIG. 10 illustrates a treatment procedure that may be employed to treat the eye.
FIG. 11 illustrates another treatment procedure that may be employed to treat the eye.

FIGS. 10 and 11 illustrate treatment procedures that may be employed to treat the eye. FIG. 10 illustrates a plurality of spaced apart fixed locations 117 about the limbus 4 of the eye that are each treated with a pair electrodes in a resistive or capacitive manner. The treatment illustrated in FIG. 10 would correspond to the treatment provided by the systems illustrated in FIGS. 3-5, 8, and 9. The plurality of spaced apart fixed locations 117 illustrated in FIG. 10 correspond to the approximate positions of the second electrodes in FIG.

3 or to the positions of the electrode pairs (i.e., electrodes 55 and 56) in FIG. 8. While electrical energy is delivered between the electrodes in the instant embodiments, the treatment of the spaced apart fixed locations 117 is similar to the treatment described in U.S. Patent Publication 2010/0076419, which is incorporated herein by reference. In delivering the treatment, the electrical energy may be delivered once to each spaced apart fixed location 117, or may be delivered multiple times to each spaced apart fixed location 117 as described below.

FIG. 11 illustrates an inductive treatment that corresponds to the treatment provided by the system illustrated in FIGS. 6 and 7. The treatment method results in a roughly circular or curved pattern of treated tissue 119 provided by the inductive current 118. The treated tissue 119 may be both above and below the limbus 4 or positioned on a single side of the limbus 4 as desired. While electrical energy is delivered by the inductive current 118, the treatment method is similar to the treatment described in U.S. Patent Publication 2015/0374539, which is incorporated herein by reference in its entirety. The treatment procedure provided by the inductive current 118 eliminates the need and time required to slide or sweep a treatment probe across the surface of the eye as in conventional procedures. The treatment of the tissue 119 may also be more precisely defined and controlled since is does not rely on a user sliding or sweeping a treatment probe across the surface of the eye. In delivering the treatment, the electrical energy may be delivered once to the tissue 119 or may be delivered multiple times to the tissue 119 as described below.

In some embodiments, the electrical energy from either the resistive, capacitive, or inductive systems may be delivered to the eye in a pulsed mode meaning that the electrodes or loop conductor may be energized for short time periods or durations to deliver electrical pulses or bursts to the eye tissue. The energizing of the electrodes or loop conductor may be referred to as an "on" time and the duration or time period that the electrodes or loop conductor is not energized may be referred to as an "off" time. Careful selection of the electrical energy pulse "on" and "off" times can avoid undesired thermal damage to target tissue by allowing the target tissue to cool during the off time before the next pulse of electrical energy is delivered during the on time. A duty cycle may be selected so that cumulative thermal buildup, caused by insufficient cooling during the off time may be avoided. Thus, damage may be reduced to a minimum level sufficient to trigger a biological response needed for lowering of intraocular pressure (IOP).

Figure 12:
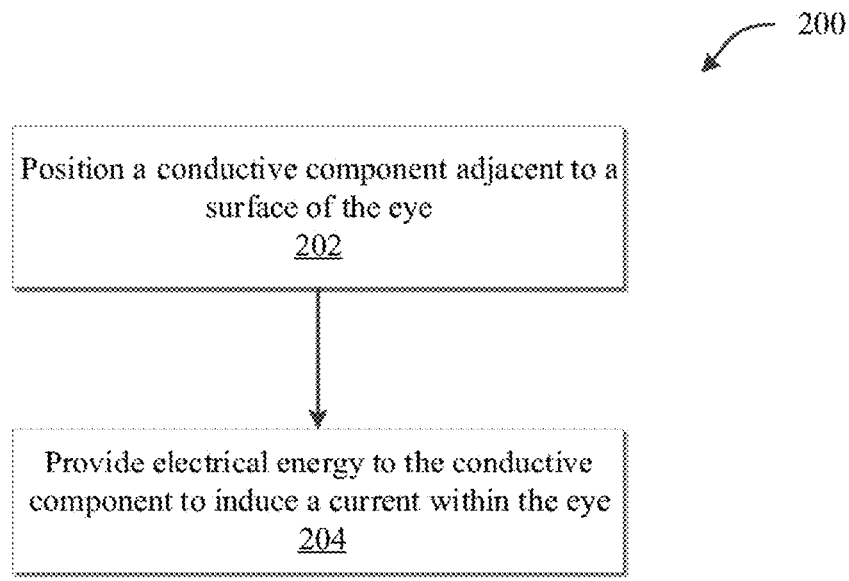
FIG. 12 illustrates a method for treating an eye of a patient.

Referring now to FIG. 12, illustrated is a method 200 for treating an eye of a patient, and in particular for treating glaucoma. At block 202, a conductive component is positioned adjacent to a surface of the eye. At block 204, electrical energy is provided to the conductive component to induce a current within the eye and thereby deliver electromagnetic energy to target tissue within the eye to therapeutically treat the target tissue.

In one embodiment, the conductive component is a loop conductor and the electrical energy is provided to induce an inductive current within the eye. In another embodiment, the conductive component is a first conductive component and the method also includes positioning a second conductive component adjacent to a surface of the eye so that the second conductive component is separated and electrically insulated from the first conductive component. In such embodiments, the electrical energy is provided to the first conductive component or the second conductive component to induce a resistive or capacitive current within the eye. The first conductive component and the second conductive component may be positioned on a lens having an inner surface that is positionable against the eye and an outer surface that is opposite the inner surface. The first conductive component and the second conductive component may be positioned on the lens so that when the lens is positioned on the eye, the first conductive component or the second conductive component is positioned adjacent or radially outward of a limbus of the eye. The first conductive component and the second conductive component may be separated by a distance that is effective to provide a desired electrical power to the eye tissues, such as the various spacing parameters described herein. For example, the first conductive component and the second conductive component may be separated by between 0.1 and 10 mm, 0.1 and 5 mm, 1 and 5 mm, 1 and 4 mm, 0.5 and 1.5 mm, 0.6 to 1.2 mm, at least 0.5 mm, and/or approximately 1.0 mm. The first conductive component and the second conductive component may form an electrode pair and the lens may include between 5 and 40 electrode pairs that are arranged and spaced apart on the lens in an annular configuration. At least some of the electrode pairs may include a sensory electrode that is configured to measure or sense one or more parameters of the target tissue or of the therapeutic treatment.

Figure 13:
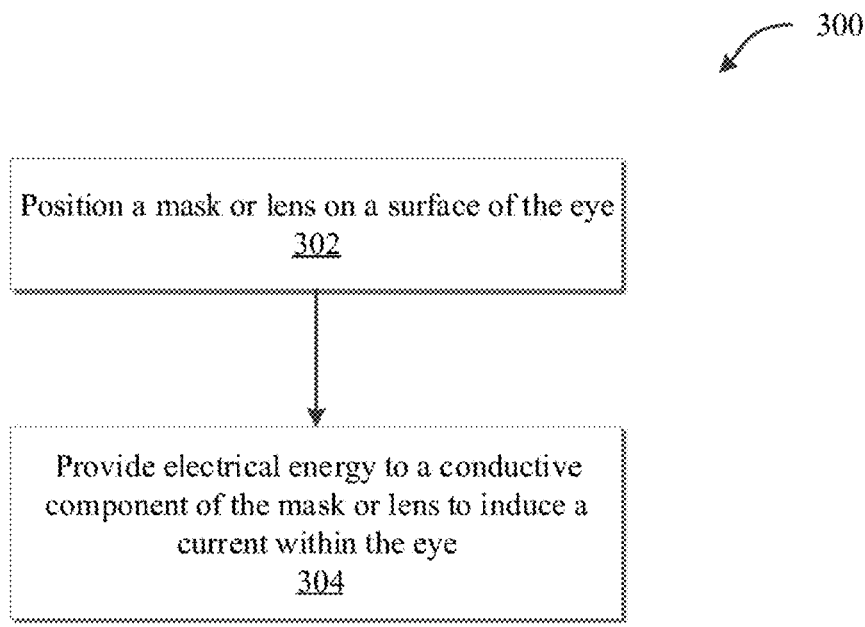
FIG. 13 illustrates another method for treating an eye of a patient.

Referring now to FIG. 13, illustrated is a method 300 for treating an eye of a patient, and in particular for treating glaucoma. At block 302, a mask or lens is positioned on a surface of the eye. The mask or lens has an inner surface that is positionable against the eye and an outer surface that is opposite the inner surface. A first conductive component is positioned on the mask or lens and a second conductive component is also positioned on the mask or lens. The first second conductive component is separated and electrically insulated from the first conductive component. The first conductive component and the second conductive component are positioned on the mask or lens so that when the mask or lens is positioned on the eye, the first conductive component or the second conductive component is positioned adjacent or radially outward form a limbus of the eye. At block 304, electrical energy is provided to the first conductive component or the second conductive component to induce a current within the eye and thereby deliver electromagnetic energy to target tissue within the eye to therapeutically treat the target tissue.

The first conductive component and the second conductive component may be separated by a distance that is effective to provide a desired electrical power to the eye tissues, such as the various spacing parameters described herein. For example, the first conductive component and the second conductive component may be separated by between 0.1 and 10 mm, 0.1 and 5 mm, 1 and 5 mm, 1 and 4 mm, 0.5 and 1.5 mm, 0.6 to 1.2 mm, at least 0.5 mm, and/or approximately 1.0 mm. The first conductive component and the second conductive component may form an electrode pair and the mask or lens may include between 5 and 40 electrode pairs that are arranged and spaced apart on the lens in an annular configuration. At least some of the electrode pairs may include a sensory electrode that is configured to measure or sense one or more parameters of the target tissue or of the therapeutic treatment.

One or more computing devices may be adapted to provide the desired functionality described herein by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method for treating glaucoma in an eye of a patient comprising:
    positioning a first conductive component adjacent to a surface of the eye;
    positioning a second conductive component adjacent to the surface of the eye so that the second conductive component is separated and electrically insulated from the first conductive component; and
    providing electrical energy to the first conductive component or the second conductive component to induce a resistive or capacitive current within the eye and thereby deliver electromagnetic energy to target tissue within the eye to therapeutically treat the target tissue; wherein:
        the first conductive component and the second conductive component are positioned on a lens having an inner surface that is positionable against the eye and an outer surface that is opposite the inner surface;
        the first conductive component and the second conductive component are positioned on the lens so that when the lens is positioned on the eye, the first conductive component or the second conductive component is positioned adjacent or radially outward of a limbus of the eye;
        the first conductive component and the second conductive component comprise an electrode pair;
        the lens includes between 5 and 40 electrode pairs that are arranged and spaced apart on the lens in an annular configuration; and
        at least some of the electrode pairs include a sensory electrode that is configured to measure or sense one or more parameters or conditions of the target tissue.

2. The method of claim 1, wherein the first conductive component and the second conductive component are separated by a distance of between 0.1 and 5 mm.

3. A method for treating glaucoma in an eye of a patient comprising:
    positioning a lens on a surface of the eye, the lens comprising an inner surface that is positionable against the eye and an outer surface that is opposite the inner surface, the lens further comprising an electrode pair that includes a first conductive component and a second conductive component, the second conductive component being separated and electrically insulated from the first conductive component;
    providing electrical energy to the first conductive component or the second conductive component to induce a resistive or capacitive current within the eye and thereby deliver electromagnetic energy to target tissue within the eye to therapeutically treat the target tissue; wherein:
        the first conductive component and the second conductive component are positioned on the lens so that when the lens is positioned on the eye, the first conductive component or the second conductive component is positioned adjacent or radially outward of a limbus of the eye; and
        the lens includes between 5 and 40 electrode pairs that are arranged and spaced apart on the lens in an annular configuration.

4. The method of claim 3, wherein the first conductive component and the second conductive component are separated by a distance of between 0.1 and 5 mm.

5. The method of claim 3, wherein at least some of the electrode pairs includes a sensory electrode that is configured to measure or sense one or more parameters or conditions of the target tissue.

* * * * *